United States Patent [19]

Paul et al.

[11] Patent Number: 5,750,771
[45] Date of Patent: May 12, 1998

[54] PROCESS FOR THE MANUFACTURE OF SEC-BUTYL ACRYLATE BY REACTION OF ACRYLIC ACID AND BUTENE ISOMERS

[75] Inventors: Jean Michel Paul, Metz; Yves Samuel, Saint-Avold; Marc Esch, Freyming-Merlebach, all of France

[73] Assignee: ELF Atochem S.A., Puteaux, France

[21] Appl. No.: 657,270

[22] Filed: Jun. 3, 1996

[30] Foreign Application Priority Data

Jun. 2, 1995 [FR] France .................... 95 06594

[51] Int. Cl.⁶ .................................................. C07C 69/52
[52] U.S. Cl. ......................................................... 560/205
[58] Field of Search .............................................. 560/205

[56] References Cited

U.S. PATENT DOCUMENTS 3,037,052  5/1962  Bortnick ........................ 260/485
4,824,998  4/1989  Inoue et al. .................... 560/205
5,138,092  8/1992  Pascual et al. ................. 560/205

FOREIGN PATENT DOCUMENTS 268999  1/1988  European Pat. Off. .

*Primary Examiner*—Paul J. Killos
*Attorney, Agent, or Firm*—Millen, White, Zelano, & Branigan, P.C.

[57] ABSTRACT

This process for the manufacture of sec-butyl acrylate by reaction of acrylic acid and at least one butene in the presence of a macroporous cationic resin containing sulphonic acid groups is characterized in that the reaction is carried out using a molar ratio of the acrylic acid to the butene(s) used which is greater than 1, the crude reaction product comprising residual acrylic acid, dissolved butene isomers, the desired sec-butyl acrylate, octenes, 2-butanol and heavy addition products, and in that the desired sec-butyl acrylate is separated from the crude reaction product.

20 Claims, No Drawings

PROCESS FOR THE MANUFACTURE OF SEC-BUTYL ACRYLATE BY REACTION OF ACRYLIC ACID AND BUTENE ISOMERS

BACKGROUND OF THE INVENTION

The present invention relates to a process for the manufacture of sec-butyl acrylate by reaction, in the presence of a sulphonic resin, between acrylic acid and butene isomers, taken individually or as mixtures, as are found, for example, in the effluent gases generated by methyl tert-butyl ether (MTBE) or ethyl tert-butyl ether (ETBE) units.

The manufacture of esters, more particularly of acrylic esters, by reaction between an olefin and a carboxylic acid is described extensively in the literature. The processes used differ by the state of the reaction medium (liquid-liquid, gas-gas or liquid-gas), by the type of catalyst used (homogeneous or heterogeneous) or by the physical state of the reactants (liquid or gas). The catalysts used in homogeneous catalysis are often strong inorganic acids.

The use of these catalysts gives rise to many problems, such as corrosion of the plants, formation of large amounts of by-products of oligomer type, for example, and laborious and difficult separations generating acidic waste.

The difficulties of separating the catalyst may readily be solved using solid catalysts.

The solid catalysts described in the literature differ according to the state of the reactants when the reaction is carried out. In the case of contact between liquid/liquid or liquid/gas reactants, those most often mentioned are: macroporous strong cationic resins containing sulphonic groups (U.S. Pat. No. 3,037,052, and U.S. Pat. No. 2,678,332; EP-A-0 445 859); zeolites (U.S. Pat. No. 4,365,084; U.S. Pat. No. 4,448,983; JP-A-03 145 440); salts of the n-dodecyl aza cycloheptan-2-one-HBr type (WO 88/02361); and caesium, rubidium and thallium salts of phosphotungstic acid (JP-A-04 139 149). The use of macroporous strong cationic resins containing sulphonic groups is the one most often mentioned. With these selective catalysts which do not generate any colored or oligomeric by-products, as is the case with inorganic acids, the problems of corrosion and of separation of the catalyst from the crude reaction product are avoided.

American patent U.S. Pat. No. 3,037,052 describes the use of sulphone-containing cationic resins as catalyst in the synthesis of secondary or tertiary alkyl esters. The synthesis of sec-butyl acrylate from 1-butene, with an acrylic acid/1-butene molar ratio of 1/1 is described in particular.

At this molar ratio, the equilibrium:

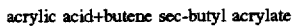

acrylic acid+butene sec-butyl acrylate is, however, not sufficiently displaced to obtain a very good conversion of the reactants used. The presence of a high content of residual acrylic acid in the crude reaction product makes the subsequent purification of sec-butyl acrylate by distillation very complex, on account of the small difference between the boiling points of the acrylic acid and the sec-butyl acrylate (respectively 141° and 131° C. at 1.01 bar (760 mmHg) and 95 and 85° C. at 0.19 bar (150 mmHg)).

In order to avoid the presence of acrylic acid at too high a content of acrylic acid in the crude reaction product, it is recommended, in European patent EP-B-0,445,859, to carry out the synthesis using a butene/acrylic acid molar ratio of greater than 1. By performing the process thus in excess butene, very good conversion of the acrylic acid is obtained and, accordingly, there is a minimum content of acrylic acid in the crude reaction product. The optimum molar ratio recommended is between 1 and 5, and with a molar ratio of 3/1 the best compromise between conversion and selectivity is obtained.

On the other hand, the fact that the process is performed in excess butene results in the formation of butene dimers (octenes), whose subsequent separation from the sec-butyl acrylate by distillation poses enormous problems on account of the small difference between their boiling points (boiling point of sec-butyl acrylate: 132° C.; boiling points of the octenes: 112°–122° C.).

SUMMARY OF THE INVENTION

Given the drawbacks which have just been described, associated with the use of a butene/acrylic acid molar ratio of greater than or equal to 1, the Applicant has discovered a means which makes it possible to surmount the drawbacks associated with the use of butene/acrylic acid molar ratios of less than 1, in other words, a means which allows the presence of a high content residual acrylic acid in the crude product of the reaction of acrylic acid and butenes in the presence of a sulphonic resin. This means is that the sec-butyl acrylate distils, in the presence of water, in the form of a heteroazeotrope which is readily separated from the acrylic acid. At a pressure of 0.19 bar (150 mmHg), the boiling points of the acrylic acid and the sec-butyl acrylate/water heteroazeotrope are 95 and 53.7° C. respectively, the composition of this heteroazeotrope by mass being, at this pressure, 73.1% sec-butyl acrylate and 26.9% water.

The fact that the process is performed in a molar excess of acrylic acid relative to the butenes has, apart from a lesser formation of octenes which are difficult to separate from the sec-butyl acrylate, the following advantages: on the one hand, it is possible to carry out the process under conditions of increased safety resulting from; the lower concentration of butenes in the medium, which butenes are readily flammable products, the decreased risk of a pressure rise in the reactor in the case of accidental polymerization and of the increase in temperature which would result therefrom, and the greater control over the introduction of the butenes into the reactor. Also, the minimum service pressure required to maintain the butenes in the liquid phase is very much lower than that which is needed when the process is performed with an excess of butenes. The safety may be further increased by introducing the butenes in the form of multi-injections.

The subject of the present invention is thus a process for the manufacture of sec-butyl acrylate by reaction of acrylic acid and at least one butene in the presence of a macroporous strong cationic resin containing sulphonic acid groups, characterized in that the reaction is carried out using a molar ratio of the acrylic acid to the butene(s) used which is greater than 1, the crude reaction product comprising residual acrylic acid, dissolved butene isomers, the desired sec-butyl acrylate, octenes, 2-butanol and heavy addition products, and in that the desired sec-butyl acrylate is separated from the crude reaction product.

The butenes used in the process according to the present invention are 1-butene, cis-2-butene and trans-2-butene, taken alone or in the form of mixtures of at least two of them. Effluent gases (referred to as Raffinates II) exiting from units for the manufacture of MTBE or ETBE and containing a fraction of about 50–90% by weight of butenes and a fraction of about 10–50% by weight of butanes, may also be reacted. In this case, the butanes will remain in the dissolved state in the crude reaction product and will be eliminated with the remaining butenes by degassing.

The acrylic acid used in the process according to the invention is either a glacial acrylic acid or a technical-grade acrylic acid.

In accordance with the invention, an acrylic acid/butene (s) molar ratio of between 1.05/1 and 10/1, and preferably of between 1.5/1 and 3/1, is generally used. The use of molar ratios greater than 3/1 is favourable for the conversion of the butenes, but is not economically advantageous.

The macroporous strong cationic resins, containing sulphonic acid groups, which can be used as catalysts for the reaction in accordance with the present invention are, in particular, those having an ionic capacity of between 0.6 and 2.5 eq/l, a pore diameter<100 nm and a specific surface of between 40 and 100 m²/g. Mention may be made, inter alia, of the resins marketed under the names Amberlyst 15 and Lewatit SPC 112 or 118. These resins are used in as anhydrous a form as possible. When they are bought in humid form, they must undergo prior drying, various modes of drying being possible, such as using a dry solvent of alcohol type, in a ventilated oven at a temperature below 110° C., or by azeotropic distillation. The maximum admissible water content in the reaction medium is about 0.5% by weight.

The reaction according to the invention is generally carried out at a temperature of between 70° and 110° C. It is important not to exceed the upper limit of 110° C. so as not to degrade the sulphonic resins. The reaction according to the invention is exothermic ($\Delta H \sim 56.43$ kJ/mol). The value of the reaction temperature is a compromise between the thermodynamic constraints and the kinetic constraints. The preferred temperature range is between 80° and 95° C.

The reaction according to the present invention is carried out at the lowest possible pressure which is compatible with maintenance of the butenes in solution. This is between 8 and 20 bar and, preferably, between 8 and 12 bar. The pressure has no effect on the reaction; it serves only to ensure the placing in contact of the reactants.

The reaction is generally carried out in the presence of at least one polymerization inhibitor, chosen preferably from hydroquinone and derivatives thereof, hydroquinone monomethyl ether, phenols having sterically bulky substituents, and phenothiazine; the content of polymerization inhibitor(s) is generally at least 50 ppm relative to the charge of acrylic acid+butene(s), the usual contents being between 100 and 1000 ppm.

The process according to the present invention may be carried out under batchwise or continuous conditions. The reaction time is generally between 1 and 5 hours, preferably between 1 and 2.5 hours, when a batchwise process is performed. Under continuous conditions, the throughput time is generally between 1 and 3 hours. These reaction times may be increased, but this increase will be detrimental to the production efficiency.

The crude reaction product contains residual acrylic acid; dissolved butene isomers; butanes if Raffinates II are used at the start; the desired sec-butyl acrylate; octenes; 2-butanol; addition products of $C_8$, $C_{12}$ acrylate type, heavy addition products of acrylic acid and of sec-butyl acrylate, and addition products of 2-butanol and sec-butyl acrylate.

In order to separate the desired sec-butyl acrylate from the crude reaction product, the following process may be carried out:

The head fraction is first removed from the crude reaction product in order to strip off the light fractions (butanes, butenes, etc.) therefrom, at a pressure generally of between 0.001 bar and 0.665 bar (1 and 500 mmHg) and preferably of between 0.066 bar and 0.133 bar (50 and 100 mmHg). The octenes, the 2-butanol and the above addition products are then eliminated by distillation at a pressure generally of between 0.013 bar and 0.665 bar (10 and 500 mmHg), preferably of between 0.066 bar and 0.266 bar (50 and 200 mmHg), as they are or in the form of an azeotrope with water. The acrylic acid and the sec-butyl acrylate are separated by heteroazeotropic distillation in the presence of water, at a service pressure generally of between 0.066 bar and 0.399 bar (50 and 300 mmHg), the mass ratio of water to the supply from the column being between 20 and 150% and preferably 50 and 100%.

The examples which follow illustrate the present invention without, however, limiting the scope thereof. In these examples, the following abbreviations have been used:

| | |
|---|---|
| AA | = acrylic acid |
| 1B | = 1-butene |
| C2B | = cis-2-butene |
| T2B | = trans-2-butene |
| B | = 1-butene + cis-2-butene + trans-2-butene |
| 2-BuA | = sec-butyl acrylate |
| HQME | = hydroquinone methyl ether |
| DIM | = octenes (the octenes, formed in small amounts during the reaction according to the invention, consist essentially of cis-5-methyl-3-heptene, trans-5-methyl-3-heptene, cis-3-methyl-3-heptene and cis-3,4-dimethyl-3-hexene) |
| 2-BuOH | = 2-butanol |
| H1 | = heavy addition product AA + 2-BuA |
| C8A | = $C_8$ acrylate |
| H2 | = heavy addition product 2-BuOH + 2-BuA |

EXAMPLES 1 TO 3

These examples demonstrate that the AA/2-BuA separation by distillation is made difficult by the fact that the boiling points of these products are very close (Examples 1 and 2). Heteroazeotropic distillation in the presence of water (Example 3) makes it possible to cary out this separation very easily.

EXAMPLE 1

A continuous distillation is carried out, at a pressure of 0.066 bar (50 mmHg), on an AA/2-BuA mixture (composition by mass: 55% AA–45% 2-BuA) on a column with Multiknit packing having an efficiency of 15 theoretical plates (3 as depletion—12 as rectification).

The rate of withdrawal is regulated as a function of a set temperature at the column head.

The conditions and results of this distillation are reported in Table 1 below.

EXAMPLE 2

Example 1 is repeated, increasing the rate of reflux and lowering the set temperature at the column head.

The conditions and results of this distillation are also reported in Table 1.

TABLE 1

| Example | Supply rate of the column (g/h) | Head rate (g/h) | Foot rate (g/h) | Rate of reflux | Head temperature (°C.) | Foot temperature (°C.) | Composition by mass at the head | | Composition by mass at the foot | | Mass ratio of the head 2-BuA/supply 2-BuA |
|---|---|---|---|---|---|---|---|---|---|---|---|
| | | | | | | | AA (%) | 2-BuA (%) | AA (%) | 2-BuA (%) | |
| 1 | 258 | 58 | 200 | 1.8/1 | 39 | 76.8 | 14 | 86 | 66 | 34 | 43 |
| 2 | 260 | 38 | 222 | 3.8/1 | 34 | 76 | 0.1 | 99.9 | 63 | 37 | 32 |

The majority of the 2-BuA is found at the foot, which is not very desirable. The quality of the pure product is obtained to the detriment of the production efficiency.

EXAMPLE 3

The AA/2-BuA mixture (composition by mass: 50% AA—50% 2-BuA) is separated by heteroazeotropic distillation in the presence of water at a pressure of 0.19 bar (150 mmHg). The column used is the same as in Examples 1 and 2. The 2-BuA distils in the form of a heteroazeotrope with water, which is separated in a decanter into two phases: an organic phase $\phi_O$ and an aqueous phase $\phi_A$, which is returned in reflux on the column.

The conditions and results of this heteroazeotropic distillation are reported in Table 2 below.

TABLE 2

| Supply rate of the column (g/h) | Rate of reflux of the aqueous phase (g/h) | Head rate (g/h) | Foot rate (g/h) | Head temperature (°C.) | Foot temperature (°C.) | Head $\phi_o$ Flow rate (g/h) | $\phi_A$ Flow rate (g/h) | Foot | Mass ratio of the $\theta_o$ 2-BuA/supply 2-BuA |
|---|---|---|---|---|---|---|---|---|---|
| 300 | 291 | 429 | 162 | 55 | 95.4 | 129 | 300 | | 85.3% |
| Composition by mass | | | | AA (%) | | 0.09 | 0.1 | 88.8 | |
| | | | | 2-BuA (%) | | 99.2 | 1 | 11 | |
| | | | | Water (%) | | 0.7 | 98.9 | 0.2 | |

The use of water as an azeotropic agent facilitates the AA/2-BuA separation and makes it possible to minimize the 2-BuA content in the foot of distillation.

EXAMPLE 4

72 g of AA stabilized with 200 ppm of HQME, 9 g of dry Amberlyst 15 resin, 29 g of 1B, as well as a complement of HQME in an amount such that the overall HQME content in the reaction medium is 700 ppm, are introduced into a 250 ml stainless steel reactor stirred by a magnetic flea. The AA/1B molar ratio is 1.9/1.

The reaction mixture is heated at 90° C. for 2 hours. The initial autogenous pressure is between 7 and 8 bar. It is adjusted to 10 bar with nitrogen and then falls gradually as the reaction proceeds.

At the end of the reaction, the composition of the crude reaction product is as follows:

| Composition of the crude reaction product | % by weight |
|---|---|
| AA | 42.6 |
| 2-BuA | 50.1 |
| Butenes | 5.6 |
| 2-BuOH | 0.03 |
| DIM | 0.8 |
| Heavy fractions | 0.8 |

The material balance values by weight are as follows:

| | |
|---|---|
| Degree of conversion of the AA | 41.2% |
| Degree of conversion of the initial AA/1B | 79% |
| Yield | 76% |
| Selectivity/AA | 95% |
| Selectivity/1B | 95% |

EXAMPLES 5 TO 8 (COMPARATIVE)

Example 4 is repeated, starting with various butene isomers, alone or as a mixture, with the butene(s)/AA molar ratios indicated in Table 3, the reaction being carried out at 80° C.

The results are also reported in Table 3.

TABLE 3

| Comparative example | Nature of the butenes | Butene(s)/ AA molar ratio | Analysis of the gases at the end of the test (%)* | | | Degree of conversion of the butenes into DIM (%) |
|---|---|---|---|---|---|---|
| | | | 1B | C2B | T2B | |
| 5 | 1B | 3.4/1 | 9.5 | 27.5 | 61.2 | 25.6 |
| 6 | C2B | 3.4/1 | 5.5 | 29.2 | 63.8 | 25.6 |
| 7 | 1B/T2B (57.1% – 41.3%)* | 2.8/1 | 6.0 | 27.7 | 63.8 | 22.6 |
| 8 | 1B/C2B/T2B (52.2% – 19.7% – 27.6%) | 3.3/1 | 6.3 | 28.7 | 63.2 | 22.5 |

*% values given by weight

The butenes isomerize on contact with the resin during the reaction. In an excess of butenes relative to the AA/butene(s) stoichiometry, and irrespective of the butene isomer used, large amounts of DIM are generated, which are subsequently very difficult to separate from the 2-BuA by distillation.

Table 4 below shows that lesser amounts of DIM are formed in the case of an AA/butenes molar ratio of greater than 1, in accordance with the invention.

EXAMPLES 9 TO 11

Example 4 is repeated, varying the AA/1B molar ratio. The reaction temperature and time are 90° C. and 2 hours respectively.

The reaction conditions and the results are reported in Table 4.

EXAMPLE 12

Example 4 is repeated, replacing the 1-butene by a Raffinate II containing:

34% by weight of butanes;

10% by weight of 1B;

36% by weight of T2B; and

20% by weight of C2B and working under the following conditions:

| Temperature | 85° C. |
|---|---|
| AA/butenes molar ratio | 1.9/1 |
| Initial pressure | 10 bar |
| Reaction time | 2 h |

At the end of the reaction, the composition of the crude reaction product is as follows:

| Composition of the crude reaction product | % by weight |
|---|---|
| AA | 34.1 |
| 2-BuA | 46.6 |
| Butenes + butanes | 18.3 |
| DIM | 0.8 |

TABLE 4

| Example | AA/1B molar ratio | Composition of the crude reaction product at the end of the reaction (% by weight) | | | | | | Degree of conversion of the reactant in deficit (%) | Yield (%) | Selectivity/ AA (%) | Selectivity/ 1B (%) |
|---|---|---|---|---|---|---|---|---|---|---|---|
| | | AA | B | 2-BuA | DIM | C8A | H1 | | | | |
| 9 (comparative) | 0.33/1 | 3.5 | 22.1 | 57.3 | 15.1 | 0.2 | 0.2 | 90 | 91.4 | 99.7 | 60 |
| 10 (comparative) | 1/55 | 18.7 | 9.3 | 65.9 | 2.8 | 0.2 | 2.2 | /AA:67 /1B:78 | /AA:64.8 /1B:67 | 96.4 | 85.3 |
| 11 | 3/1 | 43.3 | 3.8 | 50.9 | 0.7 | 0.03 | 0.4 | 84.3 | 78 | 97.4 | 93 |

The results of Comparative Example 9 confirm that an excess of 1B has a detrimental effect on the selectivity relative to 1B. In this case, a lot of DIM is formed, which is subsequently difficult to separate from the 2-BuA.

With an AA/1B molar ratio>1 (Example 11), little DIM is formed, and even very much less than in the case of an AA/1B ratio=1 (Comparative Example 10). The presence of residual AA in the crude product is not an inconvenience insofar as it can subsequently be separated from the 2-BuA by azeotropic distillation in the presence of water.

The material balance values by weight are as follows:

| Degree of conversion of the AA | 44% |
|---|---|
| Degree of conversion of the AA/butenes | 83% |
| Yield | 80.8% |
| Selectivity/AA | 97.3% |
| Selectivity/butenes | 95% |

These results agree with those found with pure 1-butene.

EXAMPLES 13 TO 17

Example 4 is repeated, working at 80° C. with an AA/1B molar ratio of 2/1 and with various commercial resins. The Amberlyst resins are marketed by the company Rohm & Haas, and the Lewatit resins by the company Bayer.

The results are reported in Table 5.

TABLE 5

| Example | Resins tested | Degree of conversion of the AA (%) | Degree of conversion of the butene (%) | Selectivity relative to the AA (%) | Selectivity relative to the 1B (%) |
|---|---|---|---|---|---|
| 13 | Amberlyst 15 | 47.5 | 79 | 99 | 99 |
| 14 | Lewatit SPC 112 | 39 | 66 | 80 | 92 |
| 15 | Lewatit SPC 118 | 29 | 51 | 91 | 94 |
| 16 | Amberlyst 39 | 35 | 62 | 91 | 97 |
| 17 | Amberlyst 36 | 35 | 63 | 95 | 92 |

EXAMPLES 18 TO 20

The reaction is carried out continuously at 80°–85° C., starting with the Raffinate used in Example 12, with an AA/butenes ratio of 2/1. The throughput time over the resin is calculated by the ratio Volume of swollen Amberlyst 15 resin in the reaction medium/Flow rate of the reactants.

The results are reported in Table 6.

The entire disclosure of all applications, patents and publications, cited above and below, and of corresponding French application 95/06954, are hereby incorporated by reference.

From the foregoing description, one skilled in the art can easily ascertain the essential characteristics of this invention, and without departing from the spirit and scope thereof, can

TABLE 6

| Example | Throughput time (min.) | Composition of the crude reaction product (% by weight) | | | | | Degree of conversion of the AA | AA consumed/ initial butenes | 2-BuA/ initial AA | 2-BuA/AA consumed |
|---|---|---|---|---|---|---|---|---|---|---|
| | | AA | Butenes + butanes | 2-BuA | DIM | Heavy AA + 2-BuA | | | | |
| 21 | 55 | 47 | 12 | 35.5 | 0.9 | 4.5 | 37 | 74 | 27 | 75 |
| 22 | 110 | 43.9 | 9.4 | 41 | 0.9 | 4.5 | 39 | 78 | 32 | 83 |
| 23 | 205 | 41 | 9.9 | 43.5 | 0.9 | 4.6 | 49.5 | 99 | 31.5 | 63 |

The results obtained under continuous conditions agree with those obtained under batchwise conditions.

EXAMPLES 24 TO 27

The reaction is carried out continuously at 80°–85° C., starting with 1-butene, varying the AA/1-butene molar ratio and with the throughput time over the resin being as defined in Examples 18 to 20.

The reaction conditions and the results are reported in Table 7.

make various changes or modifications of the invention to adapt it to various usages and conditions.

We claim:

1. A process for the manufacture of sec-butyl acrylate by reaction of acrylic acid and at least one butene in the presence of a macroporous cationic resin containing sulphonic acid groups, characterized in that the reaction is carried out using a molar ratio of the acrylic acid to the butene(s) used which is greater than 1, the crude reaction product comprising residual acrylic acid, dissolved butene isomers, the desired sec-butyl acrylate, octenes, 2-butanol

TABLE 7

| Example | AA/1B molar ratio | Through-put time (h) | Composition of the crude reaction product (% by weight) | | | | | | | Degree of conversion of the AA (%) | Degree of conversion of the 1B (%) | Butene converted into octenes/ initial 1-butene | 2-BuA/AA consumed |
|---|---|---|---|---|---|---|---|---|---|---|---|---|---|
| | | | AA | butenes | 2-BuA | DIM | H1 | H2 | C8A | (%) | (%) | (%) | (%) |
| 24 | 1.84 | 2 | 32.8 | 5.8 | 57.8 | 1.3 | 0.05 | 1.8 | 0.06 | 54 | 80.4 | 4.4 | 85.8 |
| 25 | 2.19 | 1.5 | 38.0 | 6.7 | 52.3 | 1.2 | 0.06 | 1.6 | 0.07 | 48.5 | 74.7 | 4.7 | 82.1 |
| 26 | 2.9 | 1.5 | 50.8 | 4.4 | 42.6 | 0.7 | 0.03 | 1.5 | 0.03 | 35.6 | 79.0 | 3.2 | 85.6 |
| 27 | 3.0 | 1 | 54.0 | 3.8 | 40.4 | 0.3 | 0.02 | 1.3 | 0.03 | 32.1 | 81.4 | 1.7 | 88.8 |

The preceding examples can be repeated with similar success by substituting the generically or specifically described reactants and/or operating conditions of this invention for those used in the preceding examples.

and heavy addition products, and in that the desired sec-butyl acrylate is separated from the crude reaction product by azeotropic distillation in the presence of water.

2. A process according to claim 1, characterized in that an acrylic acid/butene(s) molar ratio of between 1.05/1 and 10/1 is used.

3. A process according to claim 2, characterized in that an acrylic acid/butene(s) molar ratio of between 1.5/1 and 3/1 is used.

4. A process according to claim 1, wherein the at least one butene is 1-butene, cis-2-butene, trans-2-butene or a mixture of at least two thereof.

5. A process according to claim 1, wherein an effluent gas obtained from the manufacture of MTBE or ETBE comprises said at least one butene, said effluent containing a fraction of about 50–90% by weight of butenes and a fraction of about 10–50% by weight of butanes, and conducting the reaction with said effluent whereby the resultant crude reaction product comprises said butanes.

6. A process according to claim 1, wherein the macroporous cationic resin containing sulphonic acid groups has an ionic capacity of between 0.6 and 2.5 eq/l, a pore diameter<100 nm and a specific surface of between 40 and 100 m$^2$/g is used.

7. A process according to claim 1, wherein the reaction is carried out at a temperature of between 70° and 110° C.

8. A process according to claim 1, wherein the reaction is carried out under a pressure of between 8 and 20 bar.

9. A process according to claim 1, wherein the reaction is carried out under batchwise conditions with a reaction time of between 1 and 5 hours.

10. A process according to claim 1, wherein the reaction is carried out continuously, with a throughput time of between 1 and 3 hours.

11. A process according to claim 1, wherein the reaction is carried out in the presence of at least 50 ppm, relative to the acrylic acid+butene(s) charge, of at least one polymerization inhibitor chosen from the group consisting of hydroquinone and derivatives thereof, hydroquinone monomethyl ether, phenols having sterically bulky substituents, and phenothiazine.

12. A process according to claim 1, wherein the reaction is carried out at a temperature of between 80° and 95° C.

13. A process according to claim 1, wherein the reaction is carried out under a pressure of between 8 and 12 bar.

14. A process according to claim 12, wherein an acrylic acid/butene(s) molar ratio of between 1.05/1 and 10/1 is used.

15. A process according to claim 12, characterized in that an acrylic acid/butene(s) molar ratio of between 1.5/1 and 3/1 is used.

16. A process according to claim 1, wherein the reaction is conducted in the presence of a polymerization inhibitor.

17. A process according to claim 1, wherein the separation of the sec-butyl acrylate from the reaction product comprises a heteroazeotropic distillation in the presence of water so as to separate the acrylic acid from the sec-butyl acrylate.

18. A process according to claim 17, wherein said heteroazeotropic distillation is conducted at a pressure between 50 and 300 mmHg.

19. A process according to claim 18, wherein the sec-butyl acrylate forms a heteroazeotrope with water, said heteroazeotrope having a composition, by weight, of 73.1% sec-butyl acrylate and 26.9% water at 150 mmHg.

20. A process according to claim 1, wherein the separation of the sec-butyl acrylate from the conduction reaction product is conducted by a separation process comprising:

(a) stripping of a light fraction comprising butanes and butenes at a pressure of 50–100 mmHg;

(b) conducting an azeotropic distillation to remove water-azeotropes of octenes, 2-butanol and addition products at a pressure of 20–200 mmHg; and (c) conducting a heteroazeotropic distillation of the resultant product from step (b) at 50–300 mmHg so as to separate a water-sec-butyl acrylate heteroazeotrope from acrylic acid.

\* \* \* \* \*